(12) United States Patent
Kraushaar et al.

(10) Patent No.: US 8,303,571 B2
(45) Date of Patent: Nov. 6, 2012

(54) MULTIPLE-LINE CONNECTIVE DEVICES FOR INFUSING MEDICATION

(75) Inventors: Timothy Y. Kraushaar, Seal Beach, CA (US); Michael A. Merchant, Franklin, MA (US)

(73) Assignee: Errorless Medical, LLC, Seal Beach, CA (US)

( * ) Notice: Subject to any disclaimer, the term of this patent is extended or adjusted under 35 U.S.C. 154(b) by 81 days.

(21) Appl. No.: 12/847,935

(22) Filed: Jul. 30, 2010

(65) Prior Publication Data

US 2012/0029479 A1 Feb. 2, 2012

(51) Int. Cl.
*A61M 39/10* (2006.01)

(52) U.S. Cl. ...................................... 604/533

(58) Field of Classification Search .......... 604/246, 604/258, 284, 533, 534
See application file for complete search history.

(56) References Cited

U.S. PATENT DOCUMENTS

| | | | | |
|---|---|---|---|---|
| 4,931,049 A * | 6/1990 | Klimas | ............ | 604/165.01 |
| 5,098,405 A | 3/1992 | Peterson et al. | | |
| 5,169,385 A | 12/1992 | Turnbull | | |
| 5,250,038 A * | 10/1993 | Melker et al. | ............ | 604/264 |
| 5,273,533 A * | 12/1993 | Bonaldo | ............ | 604/83 |
| 5,300,034 A * | 4/1994 | Behnke et al. | ............ | 604/167.02 |
| 5,306,243 A * | 4/1994 | Bonaldo | ............ | 604/86 |
| 5,405,331 A * | 4/1995 | Behnke et al. | ............ | 604/167.02 |
| 5,431,185 A * | 7/1995 | Shannon et al. | ............ | 137/512.4 |
| 5,474,536 A * | 12/1995 | Bonaldo | ............ | 604/86 |
| 6,146,362 A * | 11/2000 | Turnbull et al. | ............ | 604/256 |
| 8,105,318 B2 * | 1/2012 | Copa et al. | ............ | 604/544 |
| 2004/0147915 A1* | 7/2004 | Hasebe | ............ | 606/28 |
| 2008/0039790 A1* | 2/2008 | Hasebe | ............ | 604/113 |
| 2008/0221651 A1* | 9/2008 | Dobak | ............ | 607/106 |
| 2009/0326481 A1* | 12/2009 | Swisher et al. | ............ | 604/246 |
| 2010/0280463 A1* | 11/2010 | Murayama et al. | ............ | 604/284 |
| 2010/0305492 A1* | 12/2010 | Lad et al. | ............ | 604/9 |

OTHER PUBLICATIONS

"T Connectors with Luers"; 2009 Qosina Catalog; p. 53; http://www.qosina.com/pdf/2009/T_Connectors_with_Luers.pdf.
"Y Connectors with Luers"; 2009 Qosina Catalog; pp. 54-55; http://www.qosina.com/pdf/2009/Y_Connectors_with%20_Luers.pdf.
Photographs showing Spin Lock Male Luer (2 sheets).

* cited by examiner

*Primary Examiner* — Nicholas Lucchesi
*Assistant Examiner* — Aarti B Berdichevsky
(74) *Attorney, Agent, or Firm* — Klein, O'Neill & Singh, LLP

(57) ABSTRACT

A multiple-line connective device for use in a medication infusing system includes a connective device body forming a main flow passage from an inlet to an outlet along a longitudinal axis, the main flow passage including an interior surface having a raised surface feature configured to induce turbulent liquid flow through the main flow passage. One or more branches extend from the connective device body, each defining at least one branch passage in communication with the main flow passage. Each branch passage enters the main flow passage at an angle with respect to the longitudinal axis that imparts a flow through the branch passage that has a directional component that is parallel to the longitudinal axis and in the direction from the inlet to the outlet.

12 Claims, 7 Drawing Sheets

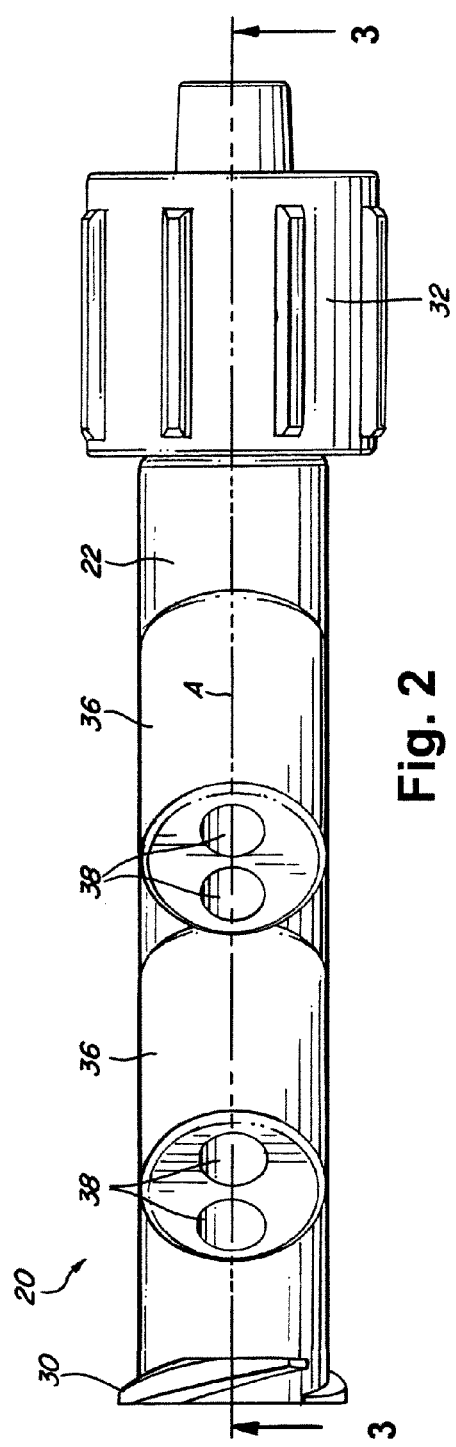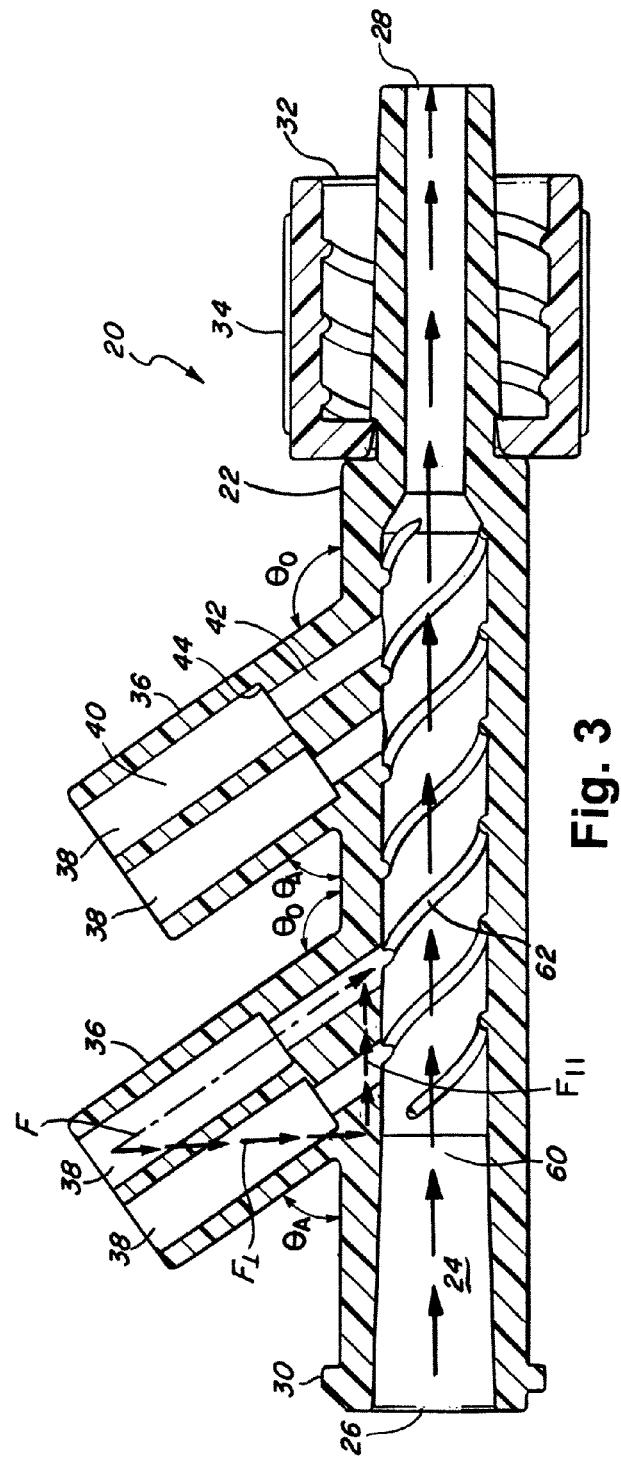

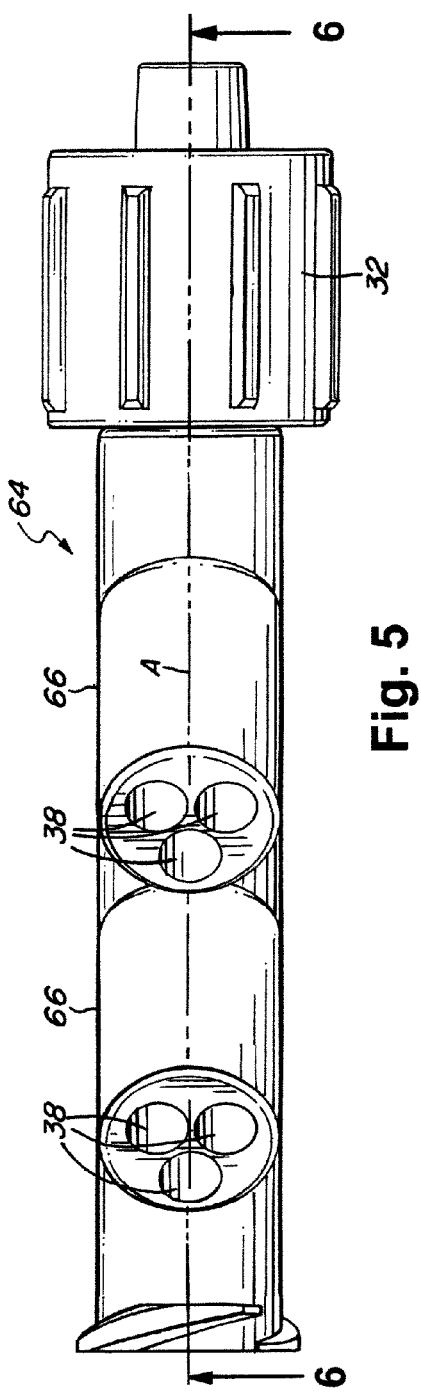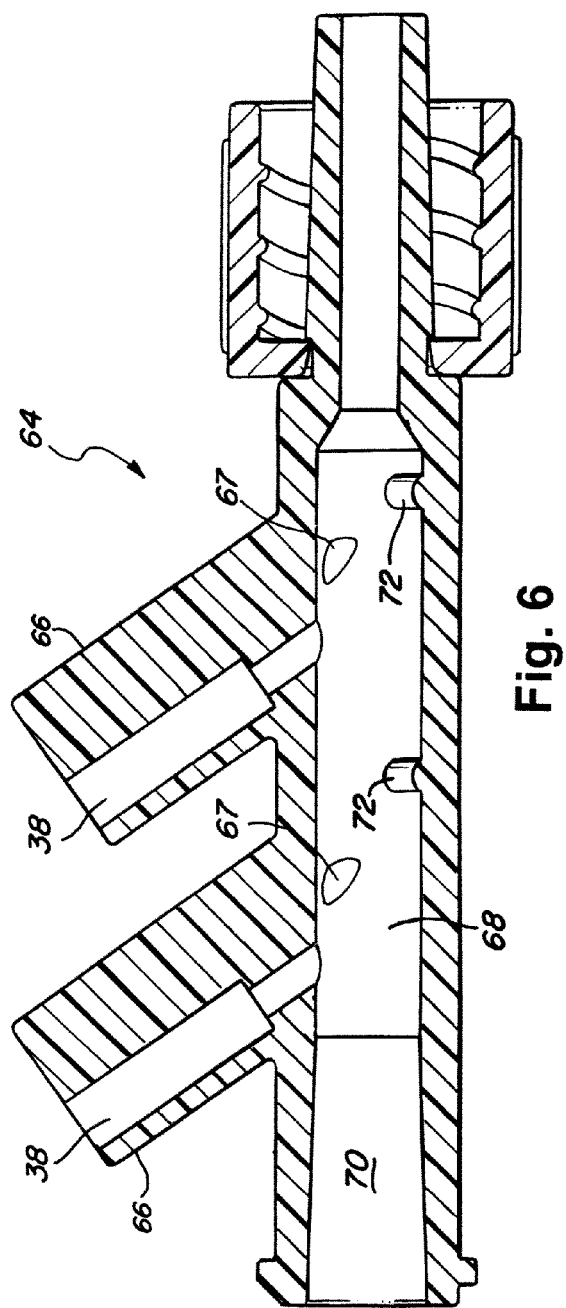
Fig. 5
Fig. 6

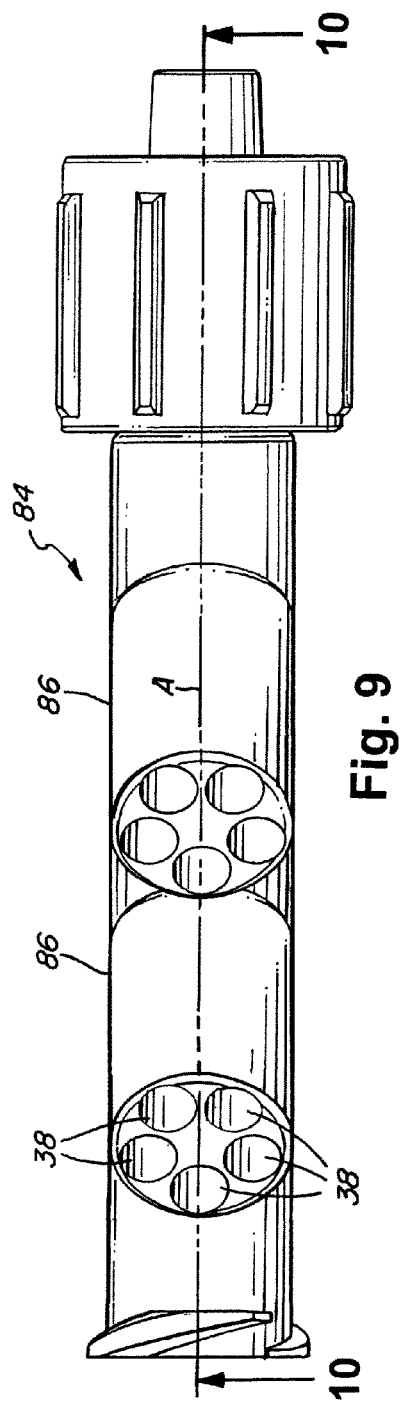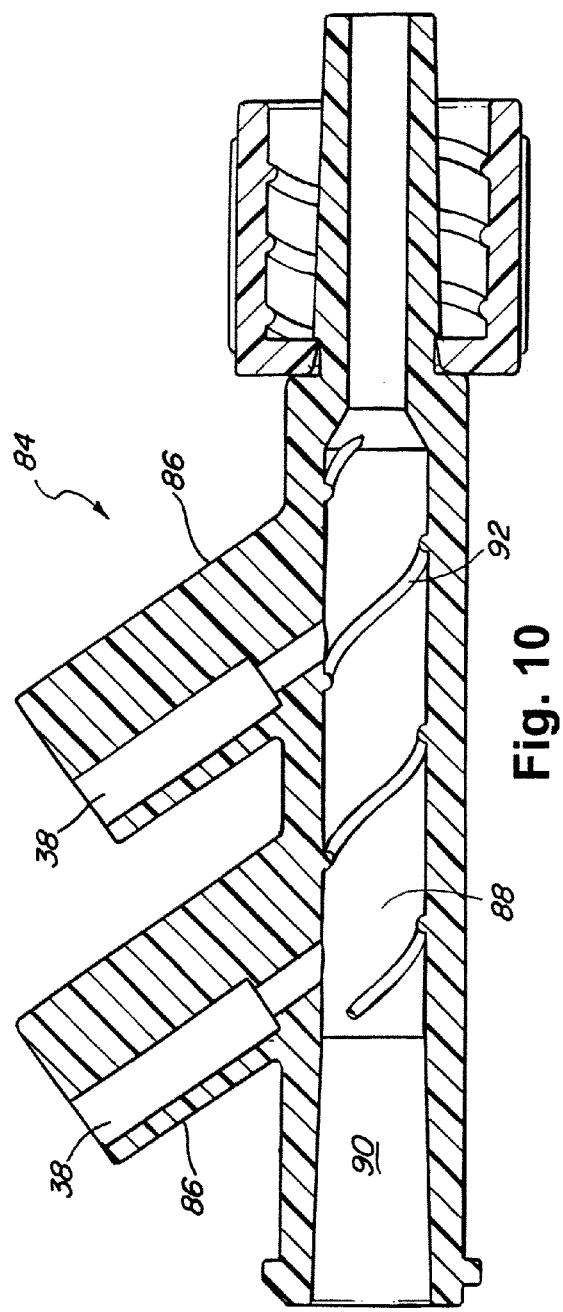

MULTIPLE-LINE CONNECTIVE DEVICES FOR INFUSING MEDICATION

CROSS-REFERENCE TO RELATED APPLICATIONS

Not applicable.

FEDERALLY SPONSORED RESEARCH OR DEVELOPMENT

Not applicable.

BACKGROUND

The present invention relates to apparatus and methods for infusing medication into a patient intravenously.

DESCRIPTION OF RELATED ART

Liquid medication is commonly infused to a patient through an intravenous (IV) line. Where more than one type of medication is needed, a multi-line connector or manifold may be used. Typically, a manifold includes a main liquid flow passage and a plurality of branch passages in fluid communication with the main passage. Intravenous liquid, such as saline, flows steadily through the main passage. When it is desired to introduce medication to the patient, the medication is introduced into the main passage through one or more of the branch passages, for example by injection with a syringe. U.S. Pat. No. 5,431,185, titled "Manifold for Infusing Medical Fluids," illustrates an example manifold. One drawback to manifolds is that they typically have considerable "dead volume." As used herein, "dead volume" refers to interior space where liquid tends to collect and stagnate. Stagnation can result in less than the intended dosage of medication reaching the patient and/or extend the time it takes for the medication to reach the patient.

An alternative to manifolds is a multi-line connector, such as the connector 100 shown in FIG. 1. As shown, the multi-line connector 100 includes a tubular body 102 defining a main flow passage 104 between an upstream end 106 and a downstream end 108. The upstream end 106 is configured to be connected to a main IV line (not shown) from a source (not shown) of primary IV fluid (e.g., saline solution). The downstream end 108 is provided with a coupling element, such as a Luer fitting 110, configured for removable connection to a device, such as a catheter (not shown) for the intravenous introduction of the IV fluids to a patient. The main flow passage 104 defines a longitudinal axis 112, and it provides a flow path for the primary IV fluid. A plurality of branches 114 extend from the tubular body 102 at approximately a right angle to the longitudinal axis 112 of the main flow passage 104. Each of the branches 114 defines a branch passage or lumen 116 that extends through the branch 114 and into the main flow passage 104. Thus, each of the branch passages or lumens 116 enters the main flow passage 104 at an angle of approximately 90 degrees to the longitudinal axis 112. While this configuration provides a reduction in dead volume as compared to a manifold, the connector 100 still creates an undesirable amount of dead volume. The configuration shown in FIG. 1 also may result in backflow through the main flow passage 104, especially if the fluid pressure through a branch passage 116 is high relative to the pressure of the flow through the main flow passage 104.

It would therefore be advantageous to provide a multi-line connective device that reduces both dead volume and backflow in the main flow passage. Furthermore, it would be advantageous for such a connective device also to promote sufficient turbulence within the main flow passage to provide good mixing of the primary IV fluid with the fluid(s) entering the main flow passage via the branch lumen(s) without significantly impairing a substantially unidirectional flow through the main flow passage.

SUMMARY

The various embodiments of the present multiple-line connective devices for infusing medication have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

In accordance with an aspect of this disclosure, a multiple-line connective device comprises a tubular body forming a main flow passage between an upstream end configured for coupling to a primary IV liquid source and a downstream end configured for connection to a device, such as a catheter, that can be coupled intravenously to a patient. The connective device further comprises at least one branch extending from the tubular body at an acute angle relative to the longitudinal axis of the main flow passage. The branch includes a branch passage or lumen in communication with the main flow passage. The branch passage provides a flow path for introducing a supplemental or secondary IV liquid into the main flow passage, with the angle of the branch passage providing flow through the branch passage that resolves into a first component directed toward the main flow passage, and a second component directed in the direction of flow through the main flow passage, thereby minimizing dead volume and promoting substantially unidirectional flow through the main flow passage with minimal backflow. The interior surface of main flow passage is provided with a raised surface feature or discontinuity that promotes sufficient turbulence in the fluid flowing therethrough to provide good mixing of the primary IV liquid with the supplemental or secondary liquid(s), without significantly impairing the substantially unidirectional flow through the main flow passage.

BRIEF DESCRIPTION OF THE DRAWINGS

The various embodiments of the present multiple-line connective devices for infusing medication now will be discussed in detail with an emphasis on highlighting the advantageous features. These embodiments depict the novel and non-obvious connective devices shown in the accompanying drawings, which are for illustrative purposes only. These drawings include the following figures, in which like numerals indicate like parts:

FIG. 2 is a top plan view of one embodiment of a multiple-line connective device in accordance with the present disclosure;

FIG. 3 is a cross-sectional view of the connective device of FIG. 2, taken through the line 3-3 in FIG. 2;

FIG. 5 is a top plan view of another embodiment of a multiple-line connective device in accordance with the present disclosure;

FIG. 6 is a cross-sectional view of the device of FIG. 5 taken through the line 6-6 in FIG. 5;

FIG. 9 is a top plan view of a further embodiment of a multiple-line connective device in accordance with the present disclosure; and FIG. 10 is a cross-sectional view of the connective device of FIG. 9 taken through the line 10-10 in FIG. 9.

DETAILED DESCRIPTION

Figure 1:
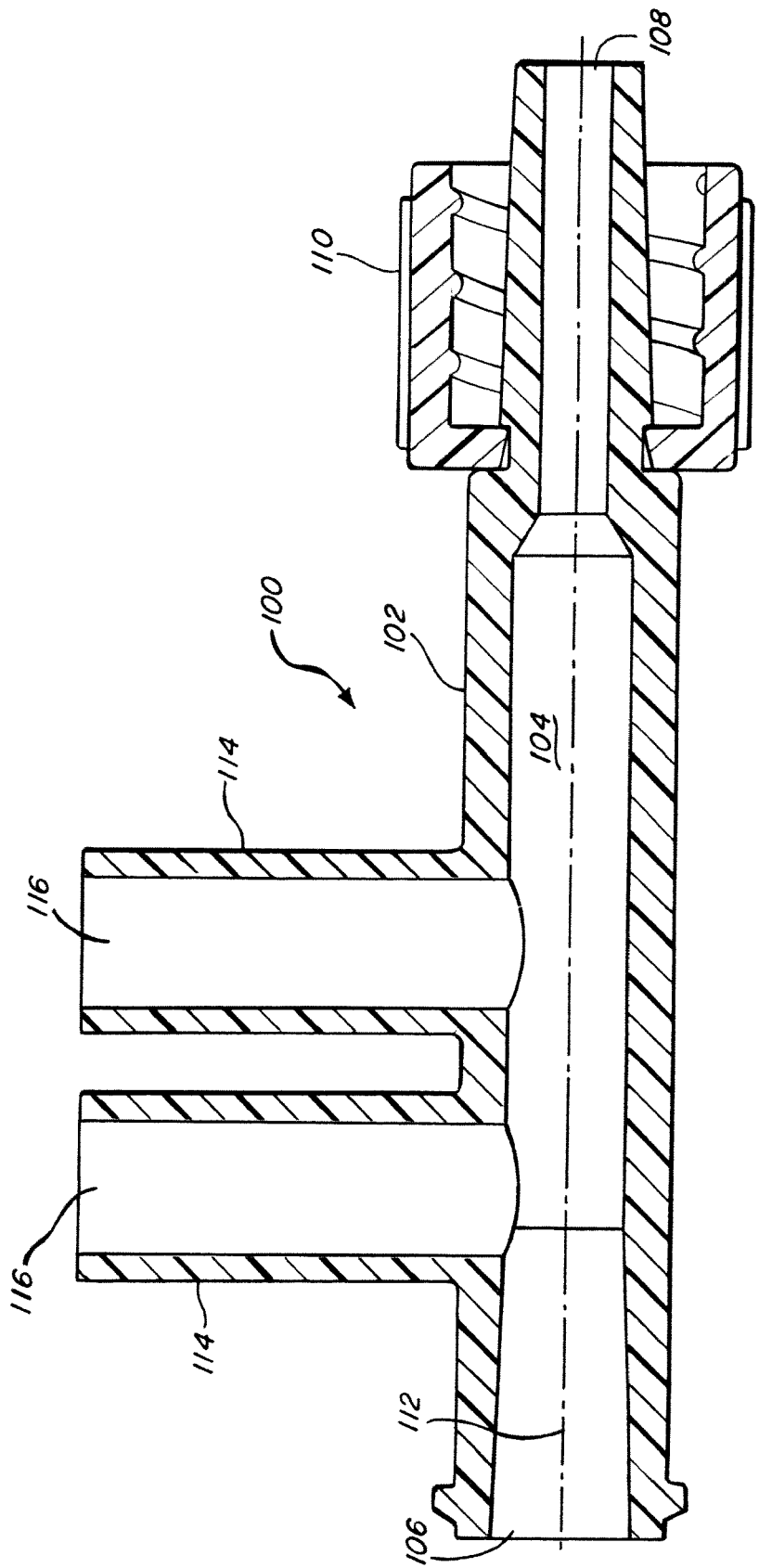
FIG. 1 is cross-sectional view of a conventional multi-line connective device, as described above.

The following detailed description describes the present embodiments with reference to the drawings. In the drawings, reference numbers label elements of the present embodiments. These reference numbers are reproduced below in connection with the discussion of the corresponding drawing features.

The embodiments of the present multiple-line connective devices for infusing medication are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unitary piece.

FIGS. 2 and 3 illustrate one exemplary embodiment of the present multiple-line connective device 20. The connective device 20 is configured for infusing a liquid medication or medicament intravenously to a patient through a venous access site (not shown). As used herein, the terms "medication" and "medicament" are meant to include any liquid that may be administered intravenously to a patient with a palliative, curative, nutritive, and/or therapeutic intent, and may include saline solution administered either by itself or as a diluent or solvent for another agent. The connective device 20 comprises a tubular body 22 defining an axial main flow passage 24 along a longitudinal axis A. The main flow passage 24 provides a flow path for a principal or primary IV liquid from an inlet 26 at the upstream end to an outlet 28 at the downstream end of the body 22. The body 22 may advantageously include a first coupling element 30 at the upstream end that is configured for attachment to a complementary coupling element on the downstream end of an IV line (not shown), and a second coupling element 32 at the downstream end that is configured for attachment to a complementary coupling element on a device, such as catheter (not shown), that is configured to be coupled intravenously to a patient (not shown) through the venous access site. In the illustrated embodiment, the first or upstream coupling element 30 is a female Luer connector, and the second or downstream coupling element 32 is a male Luer connector including a rotatable collar 34. It will be appreciated that any suitable coupling elements may be substituted for the illustrated ones.

The connective device 20 further includes first and second branches 36 extending from the connective device body 22, preferably (although not necessarily) linearly arranged on a common circumferential location around the circumference of the connective device body 22. In alternative embodiments, the branches 36 may be arranged at various locations about the circumference of the connective device body 22, such as on opposite sides. Although the exemplary embodiments illustrated herein are shown and described with two branches, it will be appreciated that any number of branches 36 may be provided.

Each branch 36 includes at least one branch lumen or passage 38 in communication with the main flow passage 24. The embodiment illustrated in FIGS. 2-4 includes two branch passages 38 in each branch 36. Other embodiments may have three branch passages (FIGS. 5-7), four branch passages (FIG. 8), and five branch passages (FIGS. 9 and 10). It will be appreciated that any number of branch passages may be provided in each of the branches 36. Each branch passage or lumen 38 provides a flow path for introducing a supplemental or secondary liquid medicament into the main flow passage 24, as described in further detail below.

Figure 4:
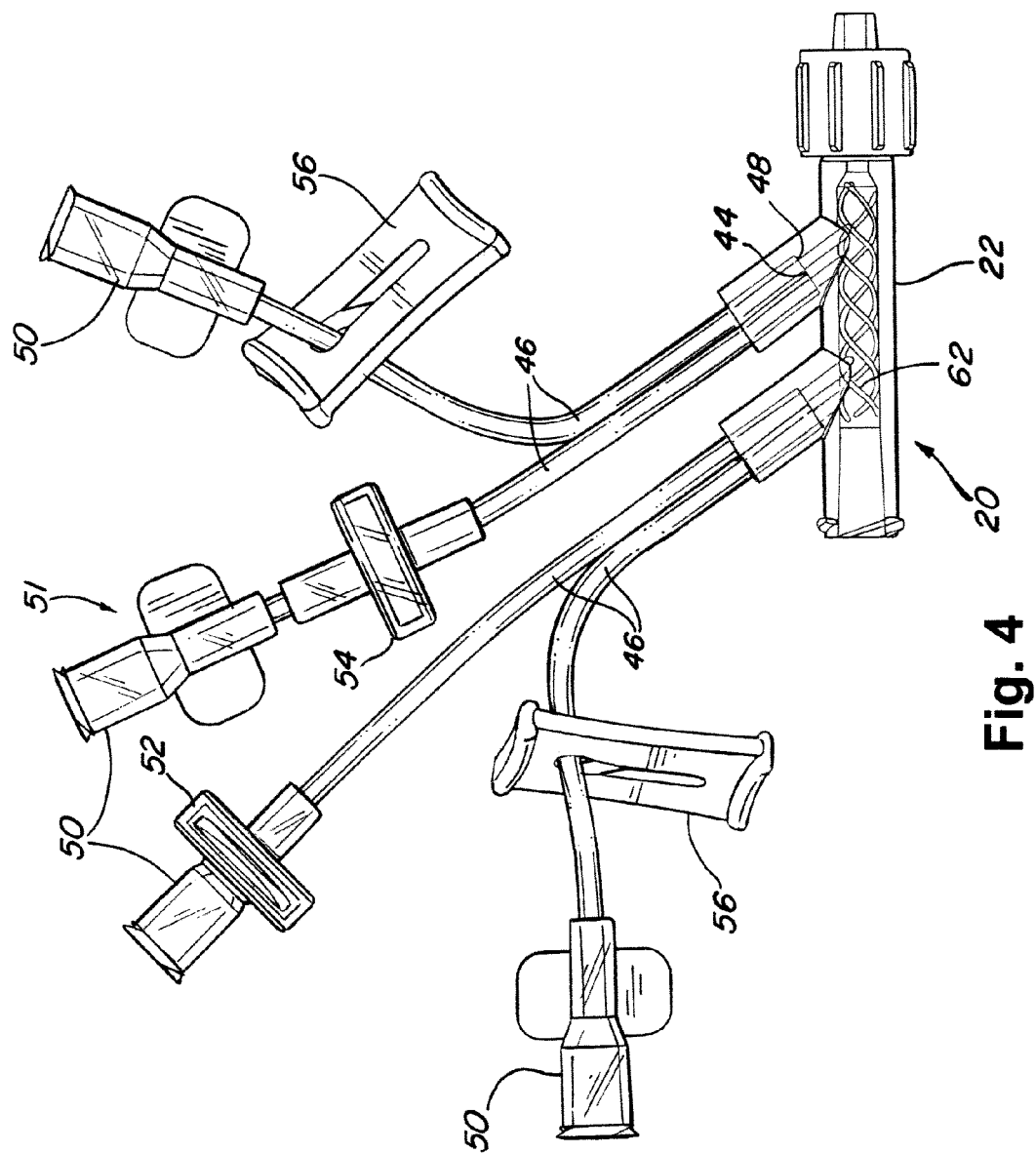
FIG. 4 is a side elevational view of the device of FIG. 2, showing a plurality of supplemental IV liquid delivery conduits attached to the device.

With reference to FIG. 3, each of the branch passages 38 may advantageously include, in certain embodiments, an upstream portion 40 that joins a downstream portion 42 at an annular shoulder 44. In embodiments in which the branch conduits 38 have upstream and downstream portions, the upstream portion 40 advantageously has an internal diameter that is greater than the internal diameter of the downstream portion 42. As shown in FIGS. 3 and 4, the upstream portion 40 of the branch liquid conduit 38 is configured to receive a branch tube 46, which is advantageously provided by standard flexible medical tubing. When received within the upstream portion 40, a downstream end 48 of the branch tubes 46 abuts the transverse annular shoulder 44 (FIG. 3). In certain embodiments, the downstream portion 42 of the branch passages 38 has an internal diameter that substantially matches the internal diameter of its associated branch tube 46, as shown in phantom in FIG. 4.

With reference to FIG. 4, an end of each of the branch tubes 46 opposite the connective device body 22 includes a mating element 50 that facilitates connection of a syringe (not shown). In the illustrated embodiment, each mating element 50 is a standard female Luer connector. However, any suitable mating element could be substituted for the illustrated Luer connectors. Collectively, each of the branch tubes 46 and its associated mating element 50 forms a supplemental liquid line 51. Connecting a syringe to one or more of the mating elements 50 enables an operator to inject an additional or supplemental medication through the associated branch tube 46 and into the main flow passage 24. Alternatively, an outlet end of an IV line containing additional or supplemental medication may be connected to one or more of the mating elements 50 to introduce the medication at a more gradual rate than injecting from a syringe. Upon reaching the main flow passage 24, the introduced supplemental or additional medication mixes with the primary IV liquid and ultimately flows to the patient through a downstream IV line (not shown) connected between the outlet 28 and a patient infusion site (not shown), which may be a venous access site.

Each mating element 50 may be clear, opaque and/or colored. In certain embodiments, the mating elements 50 associated with a single connective device 20 may have contrasting colors so that each supplemental liquid line 51 can be identified according to its color.

As shown in FIG. 4, any or all of the supplemental liquid lines 51 may optionally include a conventional one-way valve 52, 54 that enables introduction of liquid medication but resists liquid backflow. In the illustrated embodiment, a first one-way valve 52 is provided integrally with its associated mating element 50, and a second one-way valve 54 is provided inline with a branch tube 46 downstream from its associated mating element 50. As also shown in FIG. 4, any or all of the supplemental liquid lines 51 may include a slide clamp 56 for pinching off flow through the associated branch tube 46. Alternatively, a needleless swabbable valve (not shown), of a type well-known in the art, may be incorporated into the mating element 50, or located immediately downstream from the mating element 50. The one-way valves 52, 54, slide clamps 56, and the needleless swabbable valves that may be employed as discussed above are standard off-the-shelf components. Therefore, their structure will not be further described here.

With reference to FIG. 2, each of the branches 36 forms a non-orthogonal angle with the longitudinal axis A of the connective device body 22. Each of the branches 36, and thus each of the branch passages 38, forms an acute angle $\theta_A$ with the longitudinal axis A in the portion of the connective device body 22 upstream from the branch 36, and a supplementary obtuse angle $\theta_O$ with the longitudinal axis A in the portion of the connective device body 22 downstream from the branch 36. This "swept back" orientation of the branches 36 and their respective branch passages 38 relative to the longitudinal axis A of the connective device body 22 ensures that the flow F through each branch passage 38 resolves into a first directional vector or component $F_\perp$ that is perpendicular to the longitudinal axis A of the main flow passage 24, and a second directional vector or component $F_t$ that is parallel to the longitudinal axis A of the main flow passage 24, and in the same direction of flow as the flow through the main flow passage 24 (i.e., from the inlet 26 to the outlet 28). In one exemplary embodiment, the acute angle $\theta_A$ is approximately 35° and the obtuse angle $\theta_O$ is approximately 145°. In alternative embodiments, the acute angle $\theta_A$ and the supplementary obtuse angle $\theta_O$ may have any suitable magnitude. In other words, each of the branch passages 38 is configured with respect to the longitudinal axis A so as to direct the flow through the branch passage partially in the same direction as the flow through the main flow passage 24.

The flow direction F through each branch passage 38 reduces the dead volume within the connective device 20 by reducing a tendency for injected liquid to backflow within the main flow passage 24, and thereby promoting a more unidirectional overall flow through the main flow passage from the inlet 26 toward the outlet 28. In a conventional connector, such as that shown in FIG. 1, in which the branch passages are perpendicular to the main flow passage, a portion of the liquid injected into the main flow passage through the branch passages may backflow up the main flow passage due to pressure in the patient's vasculature. This backflow may create dead volume where injected secondary or supplemental medication pools in the main flow passage 24 instead of flowing to the outlet 28 and then to the patient. The illustrated connective device 20 overcomes this problem by orienting the branch passages 38 so that injected secondary or supplemental liquid is already traveling partially in the same direction as liquid within the main flow passage 24. Injection pressure thus serves only to push all of the liquid farther downstream in the main flow passage 24 against the pressure in the patient's vasculature.

With further reference to FIG. 3, an interior surface 60 of the main flow passage 24 includes a raised surface feature 62. The raised surface feature 62 is a surface discontinuity configured to induce turbulent liquid flow through the main flow passage 24, thereby to promote enhanced mixing of the primary and secondary liquids within the main flow passage 24. Specifically, the turbulent flow facilitates mixing of the secondary or supplemental liquids introduced through the supplemental lines 51 with the primary IV liquid flowing through the main flow passage 24 from the inlet 26 to the outlet 28. The enhanced mixing increases the likelihood that all of the introduced medication will flow to the patient, thereby further decreasing dead volume within the connective device 20. In the exemplary embodiment of FIGS. 3 and 4, the raised surface feature is in the form of a helix, and it may be, as shown in FIG. 4, a double helix. In alternative embodiments, the helical surface feature 62 may comprise any number of helices.

FIGS. 5 and 6 illustrate an alternative embodiment of the present multiple-line connective devices. The connective device 64 of FIGS. 5 and 6 is similar to the connective device 20 of FIGS. 2-4, except that each of its one or more branches 66 includes three branch passages 38 instead of two. Outlet openings 67 of the branch passages 38 flow into the main flow passage 24, as shown in FIG. 6. Further, with reference to FIG. 6, the interior surface 68 of the main flow passage 70 includes a plurality of noncontiguous raised surface features or discontinuities 72, rather than the raised helical surface feature 62 of the previously-described embodiment. In the illustrated embodiment, each of the noncontiguous raised surface features 72 extends circumferentially approximately one-third of the way around the interior surface 68. In alternative embodiments, the noncontiguous raised surface features 72 may extend farther around the interior surface 68, or less of the way around the interior surface 68. In still further alternative embodiments, the noncontiguous raised surface features 72 may not extend circumferentially, and may instead extend any suitable direction.

Like the raised helical surface feature 62, the plurality of noncontiguous raised surface features 72 are configured to induce turbulent liquid flow through the main flow passage 70. The noncontiguous raised surface features 72 thus generate the same advantages discussed above with respect to the raised helical surface feature 62. In some embodiments, the noncontiguous raised surface features 72 may be randomly distributed. In other embodiments, the noncontiguous raised surface features 72 may be arranged according to a set pattern. Thus, the specific shape, size, and arrangement of the raised surface features or discontinuities may be the result of a number of considerations, including, but not limited to, cost of manufacture, the amount of the mixing desired, and the physical characteristics (e.g., viscosity and miscibility) of the particular liquids to be infused in the IV system.

Figure 7:
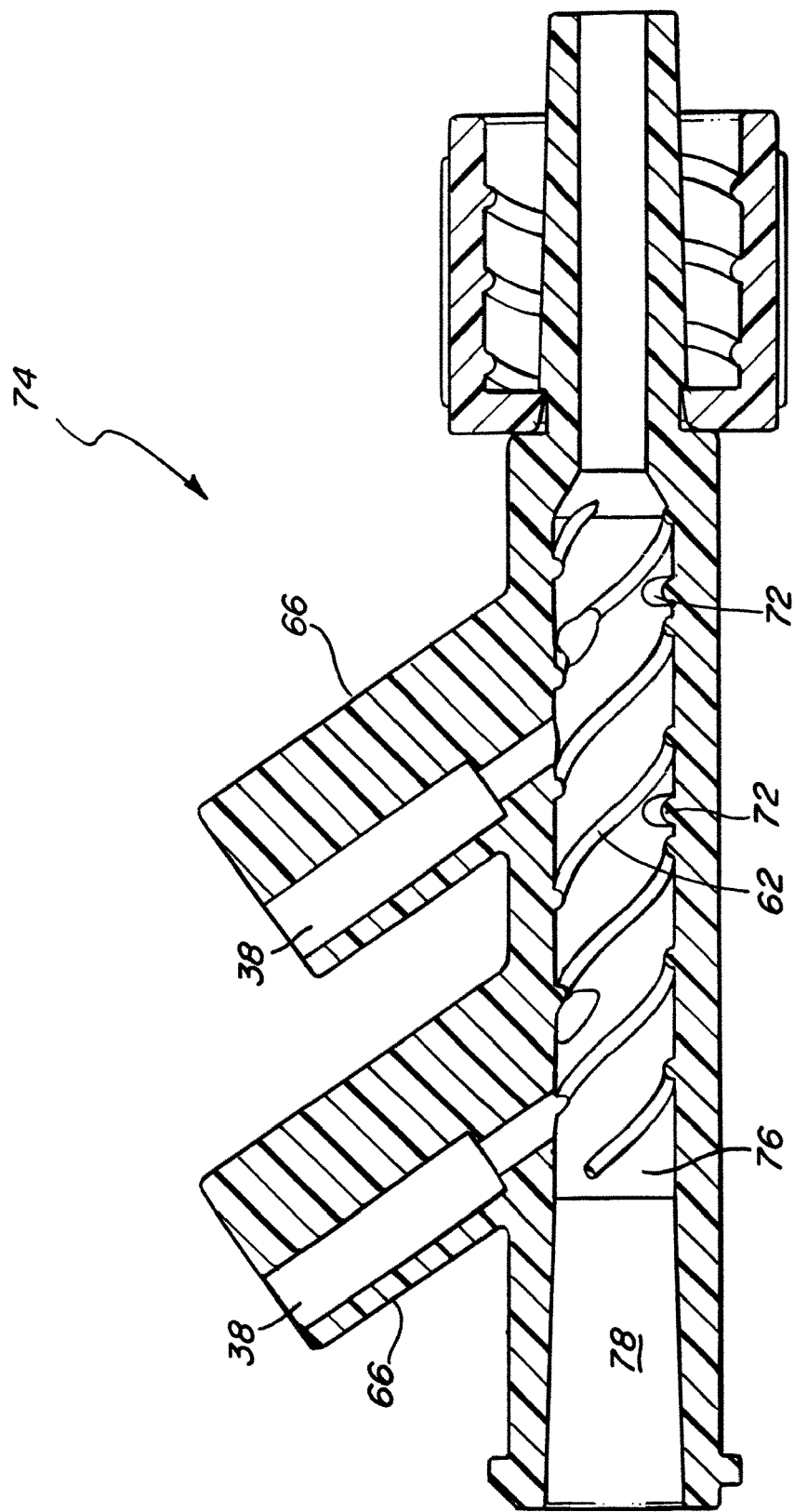
FIG. 7 is a cross-sectional view of another embodiment of a multiple-line connective device in accordance with the present disclosure.

FIG. 7 illustrates another alternative embodiment of the present multiple-line connective devices. The connective device 74 of FIG. 7 is similar to the connective device 20 of FIGS. 2-4. In the embodiment of FIG. 7, however, the interior surface 76 of the main flow passage 78 includes both a raised helical surface feature 62 and a plurality of noncontiguous raised surface features 72. As shown, all of the noncontiguous raised surface features 72 are spaced from the raised helical surface feature 62. However, in alternative embodiments some or all of the noncontiguous raised surface features 72 may overlie and/or overlap the raised helical surface feature 62. The combination of the raised helical surface feature 62 and the plurality of noncontiguous raised surface features 72 may provide enhanced turbulent liquid flow through the main flow passage 78 as compared to either of the features 62, 72 separately. The combination thus generates similar advantages as discussed above with respect to the raised helical surface feature 62.

Figure 8:
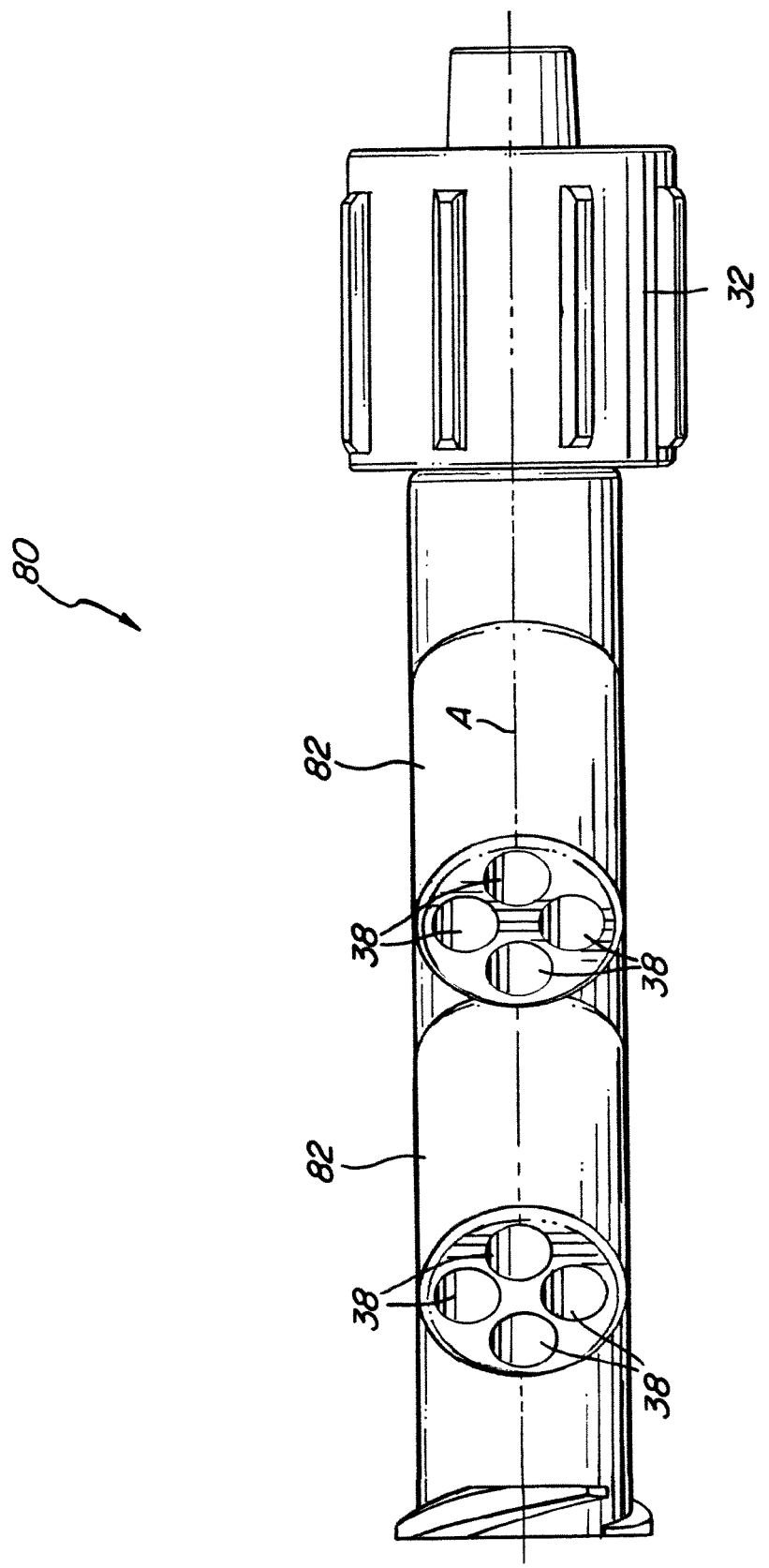
FIG. 8 is a top plan view of still another embodiment of a multiple-line connective device in accordance with the present disclosure.

FIG. 8 illustrates still another alternative embodiment of the present multiple-line connective devices. The connective device 80 of FIG. 8 is similar to the connective device 20 of FIGS. 2-4, except that each of its one or more branches 82 includes four branch passages 38 instead of two.

FIGS. 9 and 10 illustrate still another alternative embodiment of the present multiple-line connective devices. The connective device 84 of FIGS. 9 and 10 is similar to the connective device 20 of FIGS. 2-4, except that each of its one or more branches 86 includes five branch passages 38 instead of two. Further, the interior surface 88 of the main flow passage 90 includes a raised helical surface feature comprising a single helix 92, which provides the advantages discussed above with respect to the raised helical surface feature 62 of the embodiment of FIGS. 2-4.

While the embodiments described above show the same number of branch passages in each branch, it should be noted that an embodiment of the connective device in accordance with this disclosure may be made in which the respective branches define different numbers of branch passages.

The various embodiments of the present connective device provide numerous advantages. For example, the flow direction through the branch passages reduces dead volume within the main flow passage, as discussed above. Further, the raised surface features or discontinuities within the main flow passage increase turbulence within the main flow passage, which, in turn, promotes improved mixing of liquids introduced through the branch passages 38 with primary liquid in the main flow passage. The mixing further reduces dead volume within the main flow passage by making it more likely that all of the introduced medication will flow to the patient, rather than pooling in the main flow passage.

The "swept back" orientation of the branches with respect to the connective device body also facilitates connecting the outlet end of the connective device body to a downstream infusion conduit or IV. Thus, with reference to FIG. 3, the obtuse angle $\theta_O$ formed between the farthest downstream of the branches 36 and the portion of the connective device body 22 downstream from that branch creates additional room for an operator to position his or her hand around the rotatable collar 34. The additional room reduces interference between the operator's hand and the downstream branch 36 as the operator screws the rotatable collar 34 onto a mating connective device on the downstream IV line.

The various embodiments of the present connective device may be constructed of suitable materials such as medical grade plastics. Example materials include polycarbonate, acrylic, polypropylene, styrene, or any other suitable plastic material. In some embodiments the connective device may be transparent or translucent.

The above description presents the best mode contemplated for carrying out the present multiple-line connective devices for infusing medication, and of the manner and process of making and using them, in such full, clear, concise, and exact teens as to enable any person skilled in the art to which it pertains to make and use these connective devices. These connective devices are, however, susceptible to modifications and alternate constructions from that discussed above that are fully equivalent. Consequently, these connective devices are not limited to the particular embodiments disclosed. On the contrary, this disclosure should be deemed to encompass not only the exemplary embodiments described herein, but also all modifications and alternate constructions coming within the spirit and scope of the following claims.

What is claimed is:

1. A multiple-line connective device for use in a medication infusing system that includes a plurality of branch tubes having an outside diameter and an inside diameter, the connective device comprising:
a body defining a main flow passage from an inlet to an outlet along a longitudinal axis; and
a plurality of branches extending from the body, each of the branches defining within it a branch passage in communication with the main flow passage, each of the branch passages having an upstream portion having a uniform first diameter approximately equal to the outside diameter of one of the branch tubes so as to receive one of the branch tubes therein, and a downstream portion having a second diameter smaller than the first diameter and substantially equal to the inside diameter of one of the branch tubes, wherein each of the branch passages is configured to provide a flow path for liquid from one of the branch tubes into the main flow passage, such that a direction of liquid flow through each of the branch passages resolves into a first component that is perpendicular to the longitudinal axis and a second component that extends from the inlet to the outlet parallel to the longitudinal axis.

2. The connective device of claim 1, wherein an interior surface of the main flow passage includes a raised surface feature configured to induce turbulent liquid flow through the main flow passage.

3. The connective device of claim 2, wherein the raised surface feature comprises a helix.

4. The connective device of claim 2, wherein raised surface feature comprises a plurality of noncontiguous raised surface features.

5. The connective device of claim 1, wherein each of the branches includes a plurality of branch passages in communication with the main flow passage, and wherein each of the branch passages includes an upstream portion having a uniform first diameter approximately equal to the outside diameter so as to receive one of the branch tubes therein, and a downstream portion having a second diameter smaller than the first diameter and substantially equal to the inside diameter of one of the branch tubes, wherein each of the branch passages is configured to provide a flow path for liquid from one of the branch tubes into the main flow passage, such that a direction of liquid flow through each of the branch passages resolves into a first component that is perpendicular to the longitudinal axis and a second component that extends from the inlet to the outlet parallel to the longitudinal axis.

6. The connective device of claim 5, wherein each of the branch passages includes an annular shoulder at a juncture of the upstream portion and the downstream portion, wherein the annular shoulder is configured as a seat against which a proximal end of one of the branch tubes abuts when it is received in the upstream portion.

7. A multiple-line connective device for use in a medication infusing system that includes a plurality of branch tubes having an inside diameter, the connective device comprising:
a body defining a main flow passage from an inlet to an outlet along a longitudinal axis; and
a plurality of branches extending from the body, each of the branches defining within it a plurality of substantially parallel linear branch passages in communication with the main flow passage, each of the branch passages having an upstream portion having a first diameter dimensioned to receive one of the branch tubes therein, and a coaxial downstream portion opening into the main flow passage and having a second diameter smaller than the first diameter, wherein each of the branch passages is configured to provide a flow path for liquid from one of the branch tubes into the main flow passage, such that a direction of liquid flow through each of the branch passages resolves into a first component that is perpendicular to the longitudinal axis and a second component that extends from the inlet to the outlet parallel to the longitudinal axis.

8. The connective device of claim 7, wherein the second diameter is substantially equal to the inside diameter of one of the branch tubes.

9. The connective device of claim 7, wherein each of the branch passages includes an annular shoulder at a juncture of the upstream portion and the downstream portion, wherein the annular shoulder is configured as a seat against which a proximal end of one of the branch tubes abuts when it is received in the upstream portion.

10. The connective device of 7, wherein an interior surface of the main flow passage includes a raised surface feature configured to induce turbulent liquid flow through the main flow passage.

11. The connective device of claim 10, wherein the raised surface feature comprises a helix.

12. The connective device of claim 10, wherein raised surface feature comprises a plurality of noncontiguous raised surface features.

* * * * *